United States Patent
Yasuhara

(10) Patent No.: US 8,287,473 B2
(45) Date of Patent: Oct. 16, 2012

(54) MOTION ASSIST DEVICE

(75) Inventor: Ken Yasuhara, Wako (JP)

(73) Assignee: Honda Motor Co., Ltd., Tokyo (JP)

(*) Notice: Subject to any disclaimer, the term of this patent is extended or adjusted under 35 U.S.C. 154(b) by 1158 days.

(21) Appl. No.: 12/065,161

(22) PCT Filed: Jul. 12, 2006

(86) PCT No.: PCT/JP2006/313866
§ 371 (c)(1),
(2), (4) Date: Feb. 28, 2008

(87) PCT Pub. No.: WO2007/029419
PCT Pub. Date: Mar. 15, 2007

(65) Prior Publication Data
US 2009/0131839 A1    May 21, 2009

(30) Foreign Application Priority Data
Sep. 2, 2005 (JP) .................. 2005-255752

(51) Int. Cl.
*A61H 1/00* (2006.01)
*A61H 1/02* (2006.01)
*A61H 5/00* (2006.01)

(52) U.S. Cl. .................. 601/5; 600/587; 600/595

(58) Field of Classification Search ........... 601/5, 23, 601/33, 34, 35; 600/587, 595; 700/245, 700/250, 253, 254, 260, 261
See application file for complete search history.

(56) References Cited

U.S. PATENT DOCUMENTS
| | | | | |
|---|---|---|---|---|
| 3,358,678 A | * | 12/1967 | Kultsar | 601/23 |
| 2004/0102723 A1 | * | 5/2004 | Horst | 601/5 |
| 2004/0116836 A1 | * | 6/2004 | Kawai et al. | 600/595 |
| 2004/0158175 A1 | * | 8/2004 | Ikeuchi et al. | 601/5 |
| 2004/0249319 A1 | * | 12/2004 | Dariush | 601/5 |

FOREIGN PATENT DOCUMENTS
EP    1547567 A1    6/2005
(Continued)

OTHER PUBLICATIONS

Analysis of Co-emergence Process on the Human-Robot Cooperation for Walk-suppport, Takeshi Muto and Yoshihiro Miyake, vol. 38, No. 3, 316/323 (2002, English abstract included.

*Primary Examiner* — Justine Yu
*Assistant Examiner* — Raymond G Chen
(74) *Attorney, Agent, or Firm* — Rankin, Hill & Clark LLP

(57) ABSTRACT

A device for assisting a user's motion in an appropriate rhythm by bringing a user's motion rhythm close to its target rhythm while harmonizing the motion rhythms of different parts of the user's body and a rhythm for assisting the user's motion is provided. The inventive walking assist device generates a first oscillator which attains mutual entrainment with a first motion oscillator in such a way as to reflect a natural angular velocity. A new natural angular velocity is set based on a phase difference between the first motion oscillator and the first oscillator. Further, a second oscillator which oscillates in a rhythm reflecting the natural angular velocity is generated based on a second motion oscillator. An assist oscillator is then generated based on the second oscillator, and a variable force responsive to the assist oscillator is applied to the user's body.

8 Claims, 5 Drawing Sheets

FOREIGN PATENT DOCUMENTS

| | | |
|---|---|---|
| JP | 06-296705 | 10/1994 |
| JP | 08-278786 | 10/1996 |
| JP | 2003-135543 | 5/2003 |
| JP | 2004-073649 | 3/2004 |
| WO | WO 03032832 A1 * | 4/2003 |
| WO | WO 2004017890 A1 * | 3/2004 |

* cited by examiner

PHASE DIFFERENCE [rad] BETWEEN SECOND MOTION OSCILLATOR $\Phi_H$ AND ASSIST OSCILLATOR z TIME [sec]

—— SECOND MOTION OSCILLATOR $\Phi_H$
------ ASSIST OSCILLATOR z

PERIOD [s]

TIME [sec]

MOTION ASSIST DEVICE

TECHNICAL FIELD

The present invention relates to a device for assisting a user's motion, a system for controlling the device, and a program for providing a computer attached to the device with functions for controlling the device.

BACKGROUND ART

Conventionally, there has been suggested a device which assists a user in walking by applying a force assisting movements of the user's legs to the user's body parts including the legs (for example, see Japanese Patent Laid-Open No. 2003-135543). In addition, there has been suggested a system which controls the walking assist device in such a way as to add autonomy to the walking assist rhythm of the walking assist device while following changes in the user's locomotion rhythm (for example, see Japanese Patent Laid-Open No. 2004-073649).

DISCLOSURE OF THE INVENTION

Problem to be Solved by the Invention

However, if a user's arm is not impaired but his/her leg is impaired and suffering motor dysfunction and thus is difficult to perform voluntary movement, as is often the case with the users of the walking assist device, the following adverse effects are concerned.

In the case where the walking assist rhythm by the walking assist device is set to solely reflect the motion rhythm of the impaired body part, the walking assist rhythm may become inappropriate from the viewpoint of harmony with the motion rhythm of a non-impaired body part, and further from the viewpoint of harmony between the motion rhythms of the impaired and non-impaired body parts.

Further, if the walking assist rhythm by the walking assist device is set to solely reflect the motion rhythm of a non-impaired body part, then the walking assist rhythm may become inappropriate from the viewpoint of harmony with the motion rhythm of the non-impaired body part, and further from the viewpoint of harmony between the motion rhythms of the impaired and non-impaired body parts.

In view of the foregoing, it is an object of the present invention to provide a device capable of assisting a user's motion in an appropriate rhythm from the viewpoint of bringing the user's motion rhythm close to its target rhythm while totally harmonizing the motion rhythms of the different parts of the user's body and the rhythm of assisting the user's motion, a system capable of controlling the device, and a program which provides a computer attached to the motion assist device with functions for controlling the device.

Means for Solving the Problem

To achieve the above object, according to the present invention, there is provided a motion assist device for assisting a user's motion by applying a force that varies with respect to time in accordance with an assist oscillator to a user's body, which device includes: motion oscillator measurement means which measures motion oscillators responsive to movements of two different body parts of the user as first and second motion oscillators, respectively; first oscillator generation means which generates a first oscillator which attains mutual entrainment with the first motion oscillator measured by the motion oscillator measurement means in such a way as to reflect a natural angular velocity; natural angular velocity setting means which sets a new natural angular velocity on the basis of a phase difference between the first motion oscillator measured by the motion oscillator measurement means and the first oscillator generated by the first oscillator generation means; second oscillator generation means which generates a second oscillator oscillating in a rhythm reflecting the natural angular velocity set by the natural angular velocity setting means on the basis of the second motion oscillator measured by the motion oscillator measurement means; and assist oscillator generation means which generates an assist oscillator on the basis of the second oscillator generated by the second oscillator generation means.

According to the motion assist device of the present invention, firstly, a "first oscillator" is generated based on a user's "first motion oscillator". It is noted that the concept of the term "oscillate" includes a behavior where a real or virtual object shakes at substantially regular intervals and also includes changes with respect to time in a broader sense. The concept of the term "oscillator" includes an electrical signal whose value changes with respect to time, a function defined as one whose value changes with respect to time in software, and the like. The first motion oscillator corresponds to a motion oscillator responsive to movement of a user's body part, such as an arm. The first oscillator oscillates in an autonomous rhythm reflecting a natural angular velocity, while harmonizing with the rhythm of the user's "first motion oscillator" by virtue of the effect of "mutual entrainment". Meanwhile, the first oscillator is likely to have an inappropriate phase difference with respect to the user's first motion oscillator from the viewpoint of matching the user's motion rhythm with a target rhythm while harmonizing the user's motion rhythm with an assist rhythm of the motion assist device. Therefore, if the assist oscillator is directly generated from the first oscillator, the user's walking rhythm assisted by the assist oscillator might deviate from the target rhythm.

Therefore, a "new natural angular velocity" is set according to the phase difference between the user's first motion oscillator and the first oscillator. Accordingly, the new natural angular velocity becomes equivalent to an angular velocity of an appropriate oscillator from the viewpoint of assisting the user's motion in such a way as to match the user's motion rhythm with the target rhythm while harmonizing with the user's motion rhythm identified by the first motion oscillator. Thereafter, a new first oscillator is repeatedly generated in such a way as to reflect a new natural angular velocity, whereby the deviation of the phase difference between the first motion oscillator and the first oscillator from the target phase difference can be gradually reduced while harmonizing the rhythm of the first oscillator with the rhythm of the first motion oscillator.

Subsequently, a "second oscillator" is generated based on a user's "second motion oscillator". The second oscillator oscillates in a rhythm reflecting the new natural angular velocity. The second motion oscillator corresponds to a motion oscillator responsive to movement of a body part, such as a leg, different from the body part corresponding to the first motion oscillator. Then, an "assist oscillator" is generated based on the second oscillator, and a force corresponding to the assist oscillator is applied to the user's body.

As described above, the assist oscillator is generated in such a way as to reflect the motion rhythms of different body parts. Accordingly, the user's motion can be assisted so as to bring the user's motion rhythm close to a target rhythm, while harmonizing the motion rhythms of the different parts of the user's body corresponding respectively to the first and second motion oscillators. With total harmonization of the motion rhythms of the user's different body parts and the rhythm of the assist oscillator, the assist rhythm by the motion assist device becomes harmonized with the user's motion rhythm, and the user's motion rhythm also becomes harmonized with the assist rhythm by the motion assist device, and therefore, harmonization (mutual adaptation) is established between the user (human) and the device (machine).

As described above, according to the motion assist device of the present invention, the user's motion can be assisted in an appropriate rhythm from the viewpoint of bringing the user's motion rhythm close to its target rhythm, while totally harmonizing the motion rhythms of the different parts of the user's body and the rhythm of assisting the user's motion. It is noted that the user's "motion" may include various motions such as movements of the limbs associated with walking, running, manufacturing and others.

Furthermore, the motion assist device according to the present invention is characterized in that the motion oscillator measurement means measures as the first motion oscillator a motion oscillator responsive to movement of a body part to which the force is not applied, and measures as the second motion oscillator a motion oscillator responsive to movement of a body part to which the force is applied.

According to the motion assist device of the present invention, an assist oscillator is generated in such a way as to reflect both the motion rhythm of the body part to which the force is applied from the motion assist device (i.e., the rhythm of the second motion oscillator) and the motion rhythm of the body part to which the force of the motion assist device is not applied (i.e., the rhythm of the first motion oscillator).

Thus, for example, the movement of the body part that is impaired and suffering motor dysfunction and thus is assisted by the force of the motion assist device can be assisted in an appropriate rhythm from the viewpoint of overall harmony of the rhythm of the first motion oscillator responsive to movement of a non-impaired body part, the rhythm of the second motion oscillator responsive to movement of the impaired body part assisted by the force of the motion assist device, and the motion assist rhythm by the motion assist device. In this example, the effect of mutual adaptation is implemented where the movement of the non-impaired body part harmonizes with the movement of the impaired body part suffering motor dysfunction, while the movement of the impaired body part is being governed by the movement of the non-impaired body part.

Alternatively, for example, the movement of the body part that is not impaired but is assisted by the force of the motion assist device can be assisted in an appropriate rhythm from the viewpoint of overall harmony of the rhythm of the first motion oscillator responsive to movement of the body part that is impaired and suffering motor dysfunction but is not assisted by the force of the motion assist device, the rhythm of the second motion oscillator responsive to the movement of the non-impaired body part assisted by the force of the motion assist device, and the motion assist rhythm by the motion assist device. In this example, the effect of mutual adaptation is implemented where the movement of the impaired body part suffering motor dysfunction harmonizes with the movement of the non-impaired body part, while the movement of the non-impaired body part is being governed by the movement of the impaired body part.

Furthermore, the motion assist device according to the present invention is characterized in that the motion oscillator measurement means measures as the first motion oscillator a motion oscillator responsive to movement of a body part to which the force is applied, and measures as the second motion oscillator a motion oscillator responsive to movement of a body part to which the force is not applied.

According to the motion assist device of the present invention, an assist oscillator is generated in such a way as to reflect both the motion rhythm of the body part to which the force is applied from the motion assist device (i.e., the rhythm of the first motion oscillator) and the motion rhythm of the body part to which the force of the motion assist device is not applied (i.e., the rhythm of the second motion oscillator).

Thus, for example, the movement of the body part that is impaired and suffering motor dysfunction and thus is assisted by the force of the motion assist device can be assisted in an appropriate rhythm from the viewpoint of overall harmony of the rhythm of the first motion oscillator responsive to the movement of the impaired body part assisted by the force of the motion assist device, the rhythm of the second motion oscillator responsive to movement of a non-impaired body part, and the motion assist rhythm by the motion assist device. In this example, the effect of mutual adaptation is implemented where the movement of the impaired body part harmonizes with the movement of the non-impaired body part, while the movement of the non-impaired body part is being governed by the movement of the impaired body part.

Alternatively, for example, the movement of the body part that is not impaired but is assisted by the force of the motion assist device can be assisted in an appropriate rhythm from the viewpoint of overall harmony of the rhythm of the first motion oscillator responsive to the movement of the non-impaired body part assisted by the force of the motion assist device, the rhythm of the second motion oscillator responsive to the movement of the body part that is impaired and suffering motor dysfunction but is not assisted by the force of the motion assist device, and the motion assist rhythm by the motion assist device. In this example, the effect of mutual adaptation is implemented where the movement of the non-impaired body part harmonizes with the movement of the impaired body part, while the movement of the impaired body part is being governed by the movement of the non-impaired body part.

Furthermore, the motion assist device according to the present invention is characterized in that the motion oscillator measurement means measures a joint angle of an upper limb of the user or its time derivative as the first motion oscillator and a joint angle of a lower limb of the user or its time derivative as the second motion oscillator, or measures a joint angle of a lower limb of the user or its time derivative as the first motion oscillator and a joint angle of an upper limb of the user or its time derivative as the second motion oscillator.

According to the motion assist device of the present invention, the motion around the joint of the upper limb or the lower limb can be assisted in an appropriate rhythm from the viewpoint of overall harmony of the motion rhythm around the joint of the upper limb, the motion rhythm around the joint of the lower limb, and the motion assist rhythm by the motion assist device.

Furthermore, the motion assist device according to the present invention is characterized in that the second oscillator generation means generates the second oscillator oscillating in a rhythm reflecting a natural angular velocity based on a right shoulder joint angle or its time derivative serving as the first motion oscillator, on the basis of a left hip joint angle or its time derivative serving as the second motion oscillator, or generates the second oscillator oscillating in a rhythm reflecting a natural angular velocity based on a left shoulder joint angle or its time derivative serving as the first motion oscillator, on the basis of a right hip joint angle or its time derivative serving as the second motion oscillator.

At the time of motion of the user such as walking or running motion, it is desirable for the user, from the viewpoint of natural body movement, that the motion rhythm of the arm (upper limb) around the left shoulder joint and the motion rhythm of the leg (lower limb) around the right hip joint maintain an approximately constant relationship, and that the motion rhythm of the arm around the right shoulder joint and the motion rhythm of the leg around the left hip joint maintain an approximately constant relationship. That is, it is desirable for the user from the viewpoint of natural walking that the movement of the left arm harmonizes with the movement of the right leg, and that the movement of the right arm harmonizes with the movement of the left leg.

In this regard, according to the motion assist device of the present invention, the forward/backward swinging movement of the arm or the forward/backward movement of the leg can be assisted in an appropriate rhythm from the viewpoint of harmony of the motion rhythm responsive to the forward/backward swinging movement of the user's arm (particularly, the upper arm), the motion rhythm responsive to the forward/backward movement of the user's leg (particularly, the thigh) on the side opposite from the side of the arm, and the motion assist rhythm by the motion assist device.

Furthermore, the motion assist device according to the present invention is characterized in that the first oscillator generation means generates the first oscillator as an output of a first element, in accordance with a first model which represents a relationship between a plurality of virtual first elements having outputs varying according to motion oscillators, while adjusting a relationship between a plurality of first elements on the basis of part or all of scales and rhythms of the first and second motion oscillators measured by the motion oscillator measurement means and correlation thereof.

According to the motion assist device of the present invention, it is possible to cause the relationship between a plurality of actual elements concerning the user's actual motion to be reflected to the relationship between a plurality of virtual first elements in the first model. Further, the relationship between the first elements is adjusted based on part or all of the scales and rhythms of the first and second motion oscillators responsive to the movements of the different parts of the user's body and correlation thereof. Accordingly, an appropriate first oscillator can be generated in view of the relationship between the plurality of actual elements reflected to part or all of the scales and rhythms of the first and second motion oscillators and correlation thereof. For example, in the case where the left and right arms (upper limbs) are assumed as the actual elements, the first oscillator is generated in such a way as to reflect the qualitative relationship between the left and right arms such as in moving back and forth alternately or the like. Therefore, the rhythm of the assist oscillator assisting the user's motion can be made appropriate in view of the relationship concerned.

Furthermore, the motion assist device according to the present invention is characterized in that the second oscillator generation means generates the second oscillator as an output of a second element, in accordance with a second model which represents a relationship between a plurality of virtual second elements having outputs varying according to motion oscillators, while adjusting a relationship between a plurality of second elements on the basis of part or all of scales and rhythms of the first and second motion oscillators measured by the motion oscillator measurement means and correlation thereof.

According to the motion assist device of the present invention, it is possible to cause the relationship between a plurality of actual elements concerning the user's actual motion to be reflected to the relationship between a plurality of virtual second elements in the second model. Further, the relationship between the second elements is adjusted based on part or all of the scales and rhythms of the first and second motion oscillators responsive to the movements of the different parts of the user's body and correlation thereof. Accordingly, an appropriate second oscillator can be generated in view of the relationship between the plurality of actual elements reflected to part or all of the scales and rhythms of the first and second motion oscillators and correlation thereof. For example, in the case where a plurality of user's neurons are assumed as the actual elements, the second oscillator is generated in such a way as to reflect the qualitative relationship between the neurons that govern movements of the different body parts. Therefore, the rhythm of the assist oscillator assisting the user's motion can be made appropriate in view of the relationship concerned.

Furthermore, the motion assist device according to the present invention is characterized in that the natural angular velocity setting means sets a relationship between two virtual oscillators in a virtual model on the basis of a first phase difference corresponding to a phase difference between the first motion oscillator measured by the motion oscillator measurement means and the first oscillator generated by the first oscillator generation means, and then sets an angular velocity of one of the two oscillators as a new natural angular velocity in such a way as to bring a second phase difference corresponding to a phase difference between the two oscillators close to a target phase difference.

According to the motion assist device of the present invention, the relationship between the two virtual oscillators in the virtual model is set to correspond to the phase difference (first phase difference) between the user's first motion oscillator and first oscillator. Further, one of the angular velocities of the two oscillators is set as a new natural angular velocity so as to bring the phase difference (second phase difference) between the two oscillators close to a target phase difference. Accordingly, the new natural angular velocity becomes equivalent to an angular velocity of an appropriate oscillator from the viewpoint of assisting the user's motion in such a way as to match the user's motion rhythm with the target rhythm, while harmonizing with the user's motion rhythm identified by the first motion oscillator according to the target phase difference.

Furthermore, the motion assist device according to the present invention is characterized in that the natural angular velocity setting means includes: correlation coefficient setting means which sets a correlation coefficient representing a relationship between the two virtual oscillators in the virtual model on the basis of the first phase difference; first angular velocity setting means which sets an angular velocity of a virtual motion oscillator, on the basis of the correlation coefficient set by the correlation coefficient setting means, in such a way as to minimize a difference between the first phase difference and the second phase difference; and second angular velocity setting means which sets an angular velocity of a virtual assist oscillator as the new natural angular velocity, on the basis of the angular velocity set by the first angular velocity setting means, in such a way as to minimize a difference between the second phase difference and a target phase difference.

According to the motion assist device of the present invention, through setting of the correlation coefficient for the two virtual oscillators in the virtual model and the like, the angular velocity of an appropriate oscillator can be set as the new natural angle from the viewpoint of assisting the user's motion in such a way as to match the user's motion rhythm with the target rhythm while harmonizing with the user's motion rhythm identified by the first motion oscillator as described above. Accordingly, it is possible to set an assist oscillator having appropriate rhythm and scale from the viewpoint of matching the user's motion rhythm with the target rhythm corresponding to the target phase difference, while harmonizing with the user's motion rhythm identified by the motion oscillator.

Furthermore, the motion assist device according to the present invention is characterized in that the assist oscillator generation means generates an assist oscillator which includes a first assist oscillator having a first potential which brings the second motion oscillator responsive to the user's motion scale measured by the motion oscillator measurement means close to a target value responsive to a target motion scale of the user according to the second oscillator generated by the second oscillator generation means and the natural angular velocity set by the natural angular velocity setting means.

According to the motion assist device of the present invention, the "first guide oscillator" includes the first potential for bringing the second motion oscillator responsive to the user's motion scale close to its target value. The first potential is provided according to a new natural angular velocity corresponding to the angular velocity of an appropriate oscillator from the viewpoint of guiding the user's motion in such a way as to match the user's motion rhythm with the target rhythm while harmonizing with the user's motion rhythm. Therefore, as the guide oscillator including the first guide oscillator is generated, the user's motion can be guided in such a way as to harmonize the user's motion rhythm with the rhythm of the guide oscillator, to match the user's motion rhythm with the target rhythm, and to cause the value of the second motion oscillator responsive to the user's motion scale to approach the target value, or in other words, to cause the user's motion scale to approach the target scale.

Furthermore, the motion assist device according to the present invention is characterized in that the assist oscillator generation means generates the first assist oscillator which includes a product of a first coefficient responsive to the first potential as a function of the natural angular velocity set by the natural angular velocity setting means, a function of a deviation between a value of the second motion oscillator responsive to the user's motion scale and a target value, and the second oscillator, while setting the first coefficient on the basis of part or all of scales and rhythms of the first and second motion oscillators measured by the motion oscillator measurement means and correlation thereof.

According to the motion assist device of the present invention, the first assist oscillator is represented as an elastic force of an elastic element such as a virtual spring or the like which has the first coefficient responsive to the first potential as an elastic coefficient (spring coefficient) and which restores the value of the second motion oscillator responsive to the user's motion scale to the target value. The first coefficient is set based on part or all of the scales and rhythms of the first and second motion oscillators and correlation thereof. As such, the user's motion can be assisted with the rhythm and scale reflecting the properties of the elastic element of the user's body, such as the elastic force generated during the transition from the muscle contraction state to the muscle stretch state, reflected to part or all of the scales and rhythms of the first and second motion oscillators and correlation thereof.

Furthermore, the motion assist device according to the present invention is characterized in that the assist oscillator generation means generates an assist oscillator which includes a second assist oscillator having a second potential which prevents an increase in absolute value of the second motion oscillator according to the natural angular velocity set by the natural angular velocity setting means and a time derivative of the second motion oscillator responsive to the user's motion scale measured by the motion oscillator measurement means.

According to the motion assist device of the present invention, the "second guide oscillator" has the second potential for preventing an increase in absolute value of the second motion oscillator responsive to the user's motion scale. The second potential is provided according to a new natural angular velocity corresponding to the angular velocity of an appropriate oscillator from the viewpoint of guiding the user's motion in such a way as to match the user's motion rhythm with the target rhythm while harmonizing with the user's motion rhythm. Therefore, as the guide oscillator including the second guide oscillator is generated, the user's motion can be guided in such a way as to bring the user's motion scale close to the target scale, while harmonizing the user's motion rhythm with the rhythm of the guide oscillator, while matching the user's motion rhythm with the target rhythm, and while preventing the increase in absolute value of the motion oscillator according to the time derivative of the motion oscillator responsive to the user's motion scale.

Furthermore, the motion assist device according to the present invention is characterized in that the assist oscillator generation means generates the second assist oscillator which includes a product of a second coefficient responsive to the second potential as a function of the natural angular velocity set by the natural angular velocity setting means, a function of the time derivative of the second motion oscillator responsive to the user's motion scale, and the second oscillator, while setting the second coefficient on the basis of part or all of scales and rhythms of the first and second motion oscillators measured by the motion oscillator measurement means and correlation thereof.

According to the motion assist device of the present invention, the second assist oscillator is represented as a damping force of a damping element such as a virtual damper or the like which has the second coefficient responsive to the second potential as a damping coefficient (damper coefficient) and which prevents an increase in absolute value of the second motion oscillator responsive to the user's motion scale. The second coefficient is set based on part or all of the scales and rhythms of the first and second motion oscillators and correlation thereof. As such, the user's motion can be assisted with the rhythm and scale reflecting the properties of the damping element of the user's body such as the viscous force generated during the transition from the muscle stretch state to the muscle flexed state, reflected to part or all of the scales and rhythms of the first and second motion oscillators and correlation thereof.

To achieve the above object, according to the present invention, there is provided a control system which controls a device for assisting a user's motion by applying a force varying with respect to time in accordance with an assist oscillator to a user's body, which system includes: motion oscillator measurement means which measures motion oscillators responsive to movements of two different body parts of the user as first and second motion oscillators, respectively; first oscillator generation means which generates a first oscillator which attains mutual entrainment with the first motion oscillator measured by the motion oscillator measurement means in such a way as to reflect a natural angular velocity; natural angular velocity setting means which sets a new natural angular velocity on the basis of a phase difference between the first motion oscillator measured by the motion oscillator measurement means and the first oscillator generated by the first oscillator generation means; second oscillator generation means which generates a second oscillator oscillating in a rhythm reflecting the natural angular velocity set by the natural angular velocity setting means on the basis of the second motion oscillator measured by the motion oscillator measurement means; and assist oscillator generation means which generates an assist oscillator on the basis of the second oscillator generated by the second oscillator generation means.

According to the control system of the present invention, the motion assist device is controlled in such a way that the user's motion is assisted in an appropriate rhythm from the viewpoint of bringing the user's motion rhythm close to its target rhythm while totally harmonizing the motion rhythms of the different parts of the user's body and the rhythm of assisting the user's motion.

To achieve the above object, according to the present invention, there is provided a control program which provides a computer attached to a device for assisting a user's motion with functions for controlling the device, the motion assist device assisting the user's motion by applying a force varying with respect to time in accordance with an assist oscillator to a user's body, wherein the control program provides the computer with: a motion oscillator measurement function of measuring motion oscillators responsive to movements of two different body parts of the user as first and second motion oscillators, respectively; a first oscillator generation function of generating a first oscillator which attains mutual entrainment with the first motion oscillator measured by the motion oscillator measurement function in such a way as to reflect a natural angular velocity; a natural angular velocity setting function of setting a new natural angular velocity on the basis of a phase difference between the first motion oscillator measured by the motion oscillator measurement function and the first oscillator generated by the first oscillator generation function; a second oscillator generation function of generating a second oscillator oscillating in a rhythm reflecting the natural angular velocity set by the natural angular velocity setting function on the basis of the second motion oscillator measured by the motion oscillator measurement function; and an assist oscillator generation function of generating an assist oscillator on the basis of the second oscillator generated by the second oscillator generation function.

According to the control program of the present invention, the computer attached to the motion assist device is provided with the functions for controlling the motion assist device in such a way that the user's motion can be assisted in an appropriate rhythm from the viewpoint of bringing the user's motion rhythm close to its target rhythm while totally harmonizing the motion rhythms of the different parts of the user's body and the rhythm of assisting the user's motion.

BEST MODE FOR CARRYING OUT THE INVENTION

Embodiments of a motion assist device and its control system and control program according to the present invention will now be described with reference to the drawings.

Basically, subscripts L and R will be attached to parameters to make a distinction between left and right for walker's legs or the like, though the subscripts L and R may be omitted in some cases for simplicity of notation.

Figure 1:
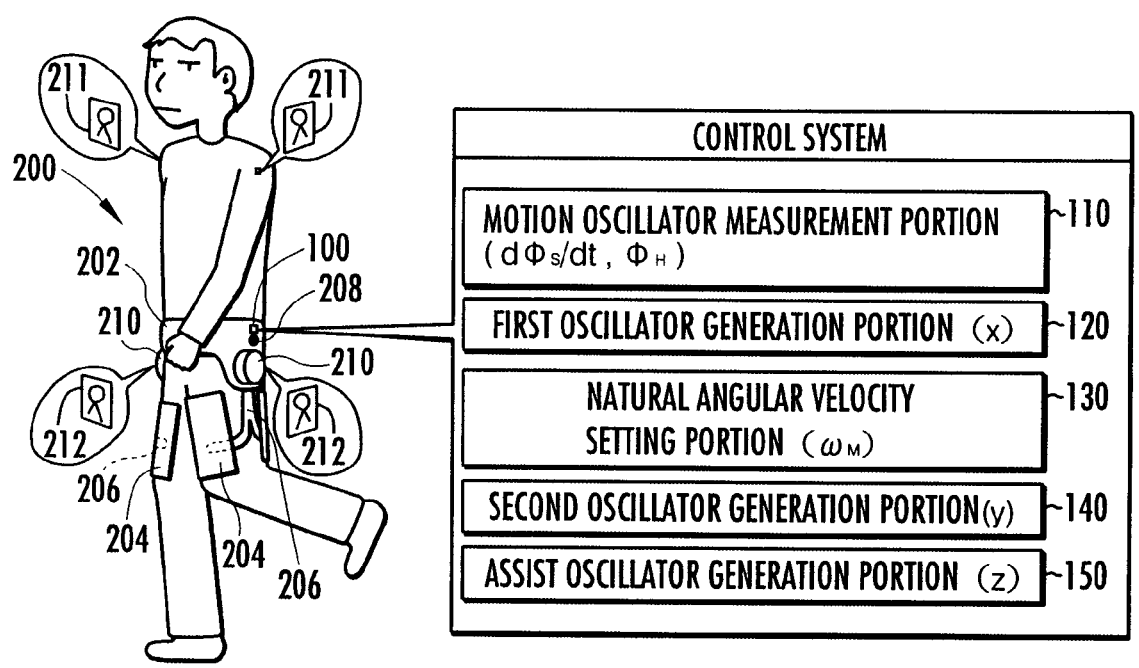
FIG. 1 is an illustrative configuration diagram showing a motion assist device and its control system according to the present invention.

A walking assist device (motion assist device) 200 shown in FIG. 1 includes a waist orthosis 202, a thigh orthosis 204, a force transmitting member 206, a battery 208, an actuator (electric motor) 210, a shoulder joint angle sensor 211, and a hip joint angle sensor 212.

The waist orthosis 202 is made of rigid and flexible materials combined with each other and it is attached to a user's waist. The thigh orthosis 204 is also made of combined rigid and flexible materials and it is attached to each of the front and back of a user's thigh. The force transmitting member 206, which is made of lightweight rigid plastic or any other material having shape retention, extends downward from each side of the user's waist along the user's corresponding thigh and then bifurcates toward the front and back of the thigh. It is connected to the actuator 210 and the respective thigh orthoses 204. The battery 208 is housed in the waist orthosis 202 (for example, fixed between a plurality of materials constituting the waist orthosis 202) and supplies electric power to the actuator 210 and the like. The actuator 210 is housed in the waist orthosis 202 and applies a force to the user's thigh via the force transmitting member 206 and the thigh orthoses 204. The shoulder joint angle sensor 211 is composed of a rotary encoder and the like provided on each of the user's left and right shoulder joints, and outputs a signal responsive to a shoulder joint angle. The hip joint angle sensor 212 is composed of a rotary encoder and the like provided on each of the sides of the user's waist, and outputs a signal responsive to a hip joint angle.

The control system shown in FIG. 1 is composed of a computer 100 as hardware housed in the waist orthosis 202, and a "control program" of the present invention as software which provides the computer 100 with functions for controlling the walking assist device 200.

The control system includes a motion oscillator measurement portion 110, a first oscillator generation portion 120, a natural angular velocity setting portion 130, a second oscillator generation portion 140, and an assist oscillator generation portion 150. Each portion is composed of a CPU, ROM, RAM or other memories, I/O and the like as hardware, and the "control program" of the present invention as software which provides various functions to the computer 100 composed of the CPU and the like (the same applies hereinafter). It is noted that the CPU and the like of each portion may be separate from those of the other portions, or may be shared among the portions.

The motion oscillator measurement portion 110 measures a shoulder joint angular velocity $d\phi_S/dt$ as a "first motion oscillator", on the basis of an output of the shoulder joint angle sensor 211. Further, the motion oscillator measurement portion 110 measures a hip joint angle $\phi_H$ as a "second motion oscillator", on the basis of an output of the hip joint angle sensor 212.

The first oscillator generation portion 120 generates a first oscillator x according to a "first model", on the basis of the shoulder joint angular velocity (first motion oscillator) $d\phi_S/dt$ measured by the motion oscillator measurement portion 110 and a natural angular velocity $\omega_M$.

The natural angular velocity setting portion 130 sets a new natural angular velocity $\omega_M$ on the basis of a phase difference (first phase difference) $\delta\theta_1$ between the shoulder joint angular velocity $d\phi_S/dt$ and the first oscillator x.

The second oscillator generation portion 140 generates a second oscillator y according to a "second model", on the basis of the hip joint angle (second motion oscillator) $\phi_H$ measured by the motion oscillator measurement portion 110 and the new natural angular velocity $\omega_M$ set by the natural angular velocity setting portion 130.

The assist oscillator generation portion 150 generates an assist oscillator z of the walking assist device 200, on the basis of the second oscillator y generated by the second oscillator generation portion 140.

The functions of the walking assist device and its control system having the above configurations will now be described with reference to FIG. 2.

Figure 2:
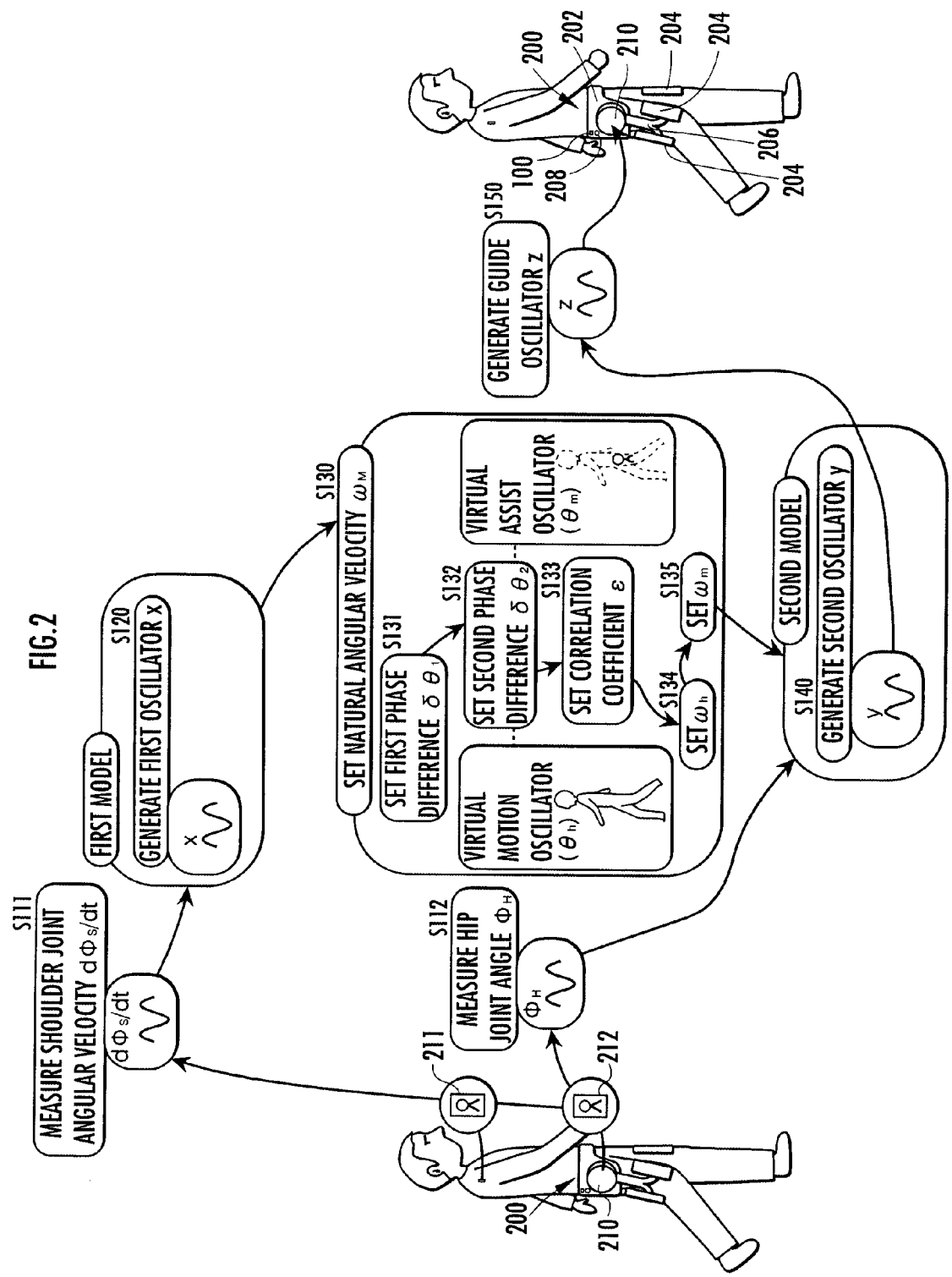
FIG. 2 is an illustrative functional diagram showing the motion assist device and its control system according to the present invention.

The motion oscillator measurement portion 110 measures user's left and right first motion oscillators (shoulder joint angular velocities) $d\phi_S/dt=(d\phi_{SL}/dt, d\phi_{SR}/dt)$ on the basis of outputs from the shoulder joint angle sensors 211 (s111 in FIG. 2). The motion oscillator measurement portion 110 measures user's left and right second motion oscillators (hip joint angles) $\phi_H=(\phi_{HL}, \phi_{HR})$ on the basis of outputs from the hip joint angle sensors 212 (s112 in FIG. 2).

The first oscillator generation portion 120 generates a first oscillator $x=(x_L, x_R)$ according to the "first model", on the basis of the first motion oscillator $d\phi_S/dt$ measured by the motion oscillator measurement portion 110 and a natural angular velocity $\omega_M=(\omega_{ML}, \omega_{MR})$ (s120 in FIG. 2). The first model represents a relationship between a plurality of virtual first elements, such as virtual left and right legs whose outputs vary according to the first motion oscillator $d\phi_S/dt$, by the van der Pol equations in the following expression (1).

$$\left(\frac{d^2 x_L}{dt^2}\right) = \xi(1-x_L^2)\left(\frac{dx_L}{dt}\right) - \omega_{ML}^2 x_L + g(x_L - x_R) + K\left(\frac{d\phi_{SL}}{dt}\right),$$
$$\left(\frac{d^2 x_R}{dt^2}\right) = \xi(1-x_R^2)\left(\frac{dx_R}{dt}\right) - \omega_{MR}^2 x_R + g(x_R - x_L) + K\left(\frac{d\phi_{SR}}{dt}\right)$$
(1)

where "$\xi$" is a coefficient (>0) set so that the first oscillator x and its one time derivative (dx/dt) move along a stable limit cycle over the x–(dx/dt) plane. "g" is a first correlation coefficient representing a correlation between the virtual left and right upper limbs (arms) (first elements) in the first model. The first correlation coefficient g may be set based on part or all of the scale (amplitude) and rhythm (frequency) of the first motion oscillator $d\phi_S/dt$, the scale and rhythm of the second motion oscillator $\phi_H$, and their correlation. "K" is a feedback coefficient. The natural angular velocity $\omega_M$ may be set arbitrarily within a range not widely deviating from an actual assist rhythm (walking motion assist rhythm) made by the walking assist device 200.

The first oscillator $x=(x_L, x_R)$ is determined/generated by the Runge-Kutta method. Components $x_L$ and $x_R$ of the first oscillator x represent virtual walking assist rhythms related to the left and right legs, respectively. In addition, by virtue of the "mutual entrainment" which is one of the properties of the van der Pol equation, the first oscillator x has a property of oscillating according to a change with respect to time in an autonomous rhythm reflecting the "natural angular velocity" $\omega_M$, while harmonizing with the rhythm of the first motion oscillator $d\phi_S/dt$ which changes with respect to time in a rhythm (angular velocity) approximately equivalent to an actual walking rhythm.

Moreover, the "first model" may be represented by a van del Pol equation different in form from the van der Pol equations in the expression (1), or may be represented by any kind of equation by which the oscillator can be generated with the mutual entrainment effect with the first motion oscillator $d\phi_S/dt$.

Furthermore, the natural angular velocity setting portion 130 sets a new natural angular velocity $\omega_M$ on the basis of the first motion oscillator $d\phi_S/dt$ measured by the motion oscillator measurement portion 110 and the first oscillator x generated by the first oscillator generation portion 120 (s130 in FIG. 2).

Specifically, for each of the left and right components, a phase difference (to be precise, a variable reflecting the phase difference) between the first motion oscillator $d\phi_S/dt$ and the first oscillator x is set as a first phase difference $\delta\theta_1$, according to the following expression (2.1) (s131 in FIG. 2).

$$\delta\theta_1 = \int dt \cdot \delta\theta\left(\frac{d\phi_s}{dt}, x\right),$$
$$\delta\theta\left(\frac{d\phi_s}{dt}, x\right) \equiv sgn(x)\left\{sgn\left(\frac{d\phi_s}{dt}\right) - sgn\left(\frac{dx}{dt}\right)\right\},$$
$$sgn(\theta) \equiv -1(\theta < o), 0(\theta = o), 1(\theta > o)$$
(2.1)

Figure 3:
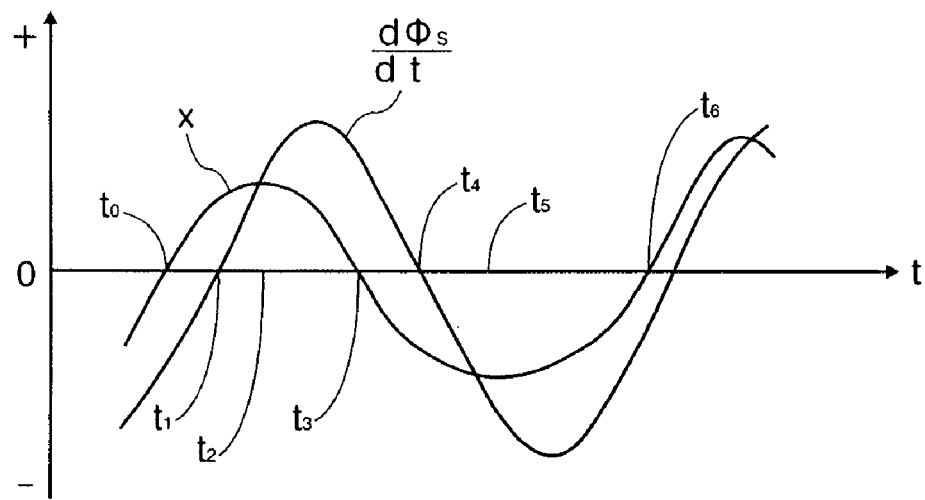
FIG. 3 is an explanatory diagram regarding a method for setting a first phase difference.

For understanding of the property of $\delta\theta$ defined by the expression (2.1), it is assumed by way of example that the shoulder joint angular velocity $d\phi_S/dt$ and the first oscillator x oscillate as shown in FIG. 3. The values "0", "positive value" and "negative value" are represented as "0", "+" and "–", respectively, for simplicity.

At time $(t_0, t_1)$, $\delta\theta$ becomes "–2" because $(d\phi_S/dt, x, dx/dt) = (–, +, +)$. At time $(t_1, t_2)$, $\delta\theta$ becomes "0" because $(d\phi_S/dt, x, dx/dt) = (+, +, +)$. At time $(t_2, t_3)$, $\delta\theta$ becomes "2" because $(d\phi_S/dt, x, dx/dt) = (+, +, –)$. At time $(t_3, t_4)$, $\delta\theta$ becomes "–2" because $(d\phi_S/dt, x, dx/dt) = (+, –, –)$. At time $(t_4, t_5)$, $\delta\theta$ becomes "0" because $(d\phi_S/dt, x, dx/dt) = (–, –, –)$. At time $(t_5, t_6)$, $\delta\theta$ becomes "2" because $(d\phi_S/dt, x, dx/dt) = (–, –, +)$.

In one period $[t_0, t_6]$ of the first oscillator x, the total sum of the accumulated time $(=(t_3–t_2)+(t_6–t_5))$ where $\delta\theta$ is "+2" is greater than the accumulated time $(=(t_1–t_0)+(t_4–t_3))$ where $\delta\theta$ is "–2". Thus, in this case, the first phase difference $\delta\theta_1$ represented by the time integral of $\delta\theta$ as in the expression (2.1) takes a positive value that becomes greater as the accumulated time where $\delta\theta$ is "+2" becomes further greater than the accumulated time where $\delta\theta$ is "–2". This means that the first motion oscillator $d\phi_S/dt$ has a phase ahead of that of the first oscillator x, which agrees with the phase relationship of these oscillators shown in FIG. 3.

Figure 4:
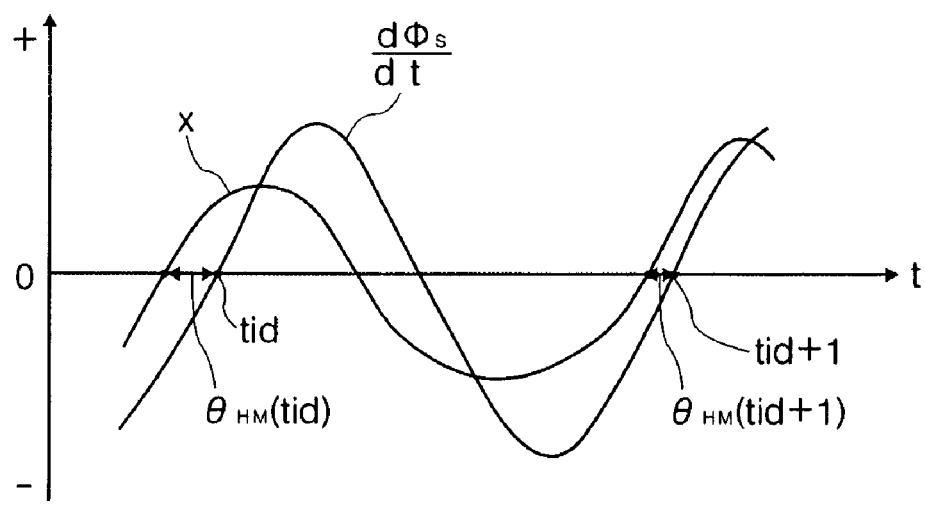
FIG. 4 is another explanatory diagram regarding the method for setting the first phase difference.

It is noted that, as shown in FIG. 4, the first phase difference $\delta\theta_1$ $(=\theta_H–\theta_M)$ may be set according to a time difference between a time point ( . . . , $t_{id}$, $t_{id+1}$, . . . ) where ($d\phi_S/dt$, $d^2\phi_S/dt^2$)=(0, +) and a time point where (x, dx/dt)=(0, +).

Subsequently, with a requirement that the first phase difference $\delta\theta_1$ was kept constant throughout the past three walking periods, a phase difference $\theta_h-\theta_m$ between a virtual motion oscillator $\theta_h$ and a virtual assist oscillator $\theta_m$ expressed by the following expression (2.4) is set as a second phase difference $\delta\theta_2$, according to a "virtual model" expressed by the following expressions (2.2) and (2.3), for each of the left and right components (s132 in FIG. 2).

$$(d\theta_h/dt) = \omega_h + \epsilon \cdot \sin(\theta_m - \theta_h) \quad (2.2)$$

$$(d\theta_m/dt) = \omega_m + \epsilon \cdot \sin(\theta_h - \theta_m) \quad (2.3)$$

$$\delta\theta_2 = \arcsin[(\omega_h - \omega_m)/2\epsilon] \quad (2.4)$$

where $\epsilon$ is a correlation coefficient between the virtual motion oscillator $\theta_h$ and the virtual assist oscillator $\theta_m$ in the virtual model. In addition, $\omega_h$ is an angular velocity of the virtual motion oscillator $\theta_h$, and $\omega_m$ is an angular velocity of the virtual assist oscillator $\theta_m$.

Subsequently, the correlation coefficient $\epsilon$ is set in such a way that a difference $\delta\theta_1 - \delta\theta_2$ between the first phase difference $\delta\theta_1$ and the second phase difference $\delta\theta_2$ is minimum (s133 in FIG. 2). Specifically, for each of the left and right components, the correlation coefficient E is sequentially set in the times ( . . . , $t_{id-1}$, $t_{id}$, $t_{id+1}$, . . . ) where ($d\phi_S/dt$, $d^2\phi_S/dt^2$)=(0, +) (see FIG. 4), according to the following expression (2.5).

$$\epsilon(t_{id+1}) = \epsilon(t_{id}) - \eta\{V(t_{id+1}) - V(t_{id})\}/\{\epsilon(t_{id}) - \epsilon(t_{id-1})\}, \quad (2.5)$$

$$V(t_{id+1}) \equiv (1/2)\{\delta\theta_1(t_{id+1}) - \delta\theta_2(t_{id})\}^2$$

where the components in $\eta=(\eta_L, \eta_R)$ are coefficients representing the stability of the potential $V=(V_L, V_R)$ which brings the left and right components of the first phase difference $\delta\theta_1$ close to those of the second phase difference $\delta\theta_2$.

Subsequently, on the basis of the correlation coefficient $\epsilon$, on the condition that the natural angular velocity $\omega_m$ of the virtual assist oscillator $\theta_m$ is kept constant, an angular velocity $\omega_h$ of the virtual motion oscillator $\theta_h$ is set according to the following expression (2.6), for each of the left and right components, in such a way that the components of the difference $\delta\theta_1 - \delta\theta_2$ between the first and second phase differences are minimum (s134 in FIG. 2).

$$\omega_h(t_{id}) = -\alpha \int dt \cdot [4\epsilon(t_{id})^2 - \{\omega_h(t) - \omega_m(t_{id})\}^2]^{1/2} \times \quad (2.6)$$

$$\sin[\arcsin\{(\omega_h(t) - \omega_m(t_{id-1}))/2\epsilon(t_{id})\} - \theta_{HM}(t_{id})])$$

where the components of $\alpha=(\alpha_L, \alpha_R)$ are coefficients representing the stability of a system.

Subsequently, for each of the left and right components, the angular velocity $\omega_m$ of the virtual assist oscillator $\theta_m$ is set as a new natural angular velocity $\omega_M$ on the basis of the angular velocity $\omega_h$ of the virtual motion oscillator $\theta_H$ (s135 in FIG. 2). Specifically, the angular velocity $\omega_m=(\omega_{mL}, \omega_{mR})$ of the virtual assist oscillator $\theta_m$ is set according to the following expression (2.7), for each of the left and right components, in such a way that the second phase difference $\delta\theta_2$ approaches a target phase difference $\delta\theta_0$.

$$\omega_m(t_{id}) = \beta \int dt \cdot ([4\epsilon(t_{id})^2 - \{\omega_h(t_{id}) - \omega_m(t)\}^2) \times \quad (2.7)$$

$$\sin[\arcsin\{(\omega_h(t_{id}) - \omega_m(t))/2\epsilon(t_{id})\} - \delta\theta_0])$$

where the components of $\beta=(\beta_L, \beta_R)$ are coefficients representing the stability of a system.

Subsequently, the second oscillator generation portion 140 generates a second oscillator $y=(y_{L+}, y_{L-}, y_{R+}, y_{R-})$ according to a "second model", on the basis of the second motion oscillator (hip joint angle) $\phi_H$ measured by the motion oscillator measurement portion 110 and the new natural angular velocity $\omega_M$ set by the natural angular velocity setting portion 130 (s140 in FIG. 2). The second model represents a relationship between a plurality of virtual second elements, such as a plurality of virtual neural elements or the like, whose outputs vary according to the second motion oscillator $\phi_H$. More specifically, the second model is expressed by the following simultaneous differential equations (3), which includes: a state variable $u_i$ (i=L+, L-, R+, R-) corresponding to changes in membrane potential of neural elements L+ and L- which govern the motions of the left thigh in the bending direction (forward) and in the stretching direction (backward), respectively, and neural elements R+ and R- which govern the motions of the right thigh in the bending direction and in the stretching direction, respectively; and a self-control factor $v_i$ reflecting an adaptive effect of the neural element i.

$$\tau_{1L+} \cdot \frac{du_{L+}}{dt} = \quad (3)$$
$$-u_{L+} + w_{L+/L-}y_{L-} + w_{L+/R+}y_{R+} - \lambda_L v_{L+} f_1(\omega_{ML}) + f_2(\omega_{ML})K(\phi_{HL}),$$

$$\tau_{1L-} \cdot \frac{du_{L-}}{dt} = -u_{L-} + w_{L-/L+}y_{L+} + w_{L-/R-}y_{R-} -$$
$$\lambda_L v_{L-} + f_1(\omega_{ML}) + f_2(\omega_{ML})K(\phi_{HL}),$$

$$\tau_{1R+} \cdot \frac{du_{R+}}{dt} = -u_{R+} + w_{R+/L+}y_{L+} + w_{R+/R-}y_{R-} -$$
$$\lambda_R v_{R+} + f_1(\omega_{MR}) + f_2(\omega_{MR})K(\phi_{HR}),$$

$$\tau_{1R-} \cdot \frac{du_{R-}}{dt} = -u_{R-} + w_{R-/L-}y_{L-} + w_{R-/R+}y_{R+} -$$
$$\lambda_R v_{R-} + f_1(\omega_{MR}) + f_2(\omega_{MR})K(\phi_{HR}),$$

$$\tau_{2i} \cdot \frac{dv_i}{dt} = -v_i + y_i,$$

$$y_i = \max(0, u_i)$$

where $\tau_{1i}$ is a time constant which defines a variation character of the state variable $u_i$ and it has a dependence on the new natural angular velocity $\omega_M$ as shown by the following expression (3.1) for each of the left and right components.

$$\tau_{1i} \equiv t(\omega_{ML})/\omega_{ML} - \gamma_L (i=L+, L-), \text{ or}$$

$$t(\omega_{MR})/\omega_{MR} - \gamma_R (i=R+, R-) \quad (3.1)$$

where $t(\omega)$ is a coefficient having a dependence on $\omega$. $\gamma=(\gamma_L, \gamma_R)$ is a constant.

In addition, $\tau_{2i}$ is a time constant which defines a variation character of the self-control factor $v_i$. Moreover, $w_{i/j}$ (<0) is a second correlation coefficient (constant) representing a relationship between a plurality of virtual second elements (neural elements) i and j. The second correlation coefficient $w_{i/j}$ may be set based on part or all of the scale (amplitude) and rhythm (frequency) of the first motion oscillator (shoulder joint angular velocity) $d\phi_S/dt$, the scale and rhythm of the second motion oscillator (hip joint angle) $\omega_H$, and their correlation. "$\lambda_L$" and "$\lambda_R$" are habituation coefficients. K is a feedback coefficient responsive to the hip joint angle $\phi_H$.

"$f_1$" and "$f_2$" are functions defined by the following expressions (3.2) and (3.3), respectively.

$$f_1(\omega) = c \cdot \omega (c > 0) \tag{3.2}$$

$$f_2(\omega) = c_0 + c_1 \omega + c_2 \omega^2 \tag{3.3}$$

The coefficients $c$, $c_0$, $c_1$, $c_2$ of $f_1(\omega_M)$ and $f_2(\omega_M)$, functions of the natural angular velocity $\omega_M$, may be set as coefficients corresponding to part or all of the scale (amplitude) and rhythm (frequency) of the first motion oscillator (shoulder joint angular velocity) $d\phi_S/dt$, the scale and rhythm of the second motion oscillator (hip joint angle) $\phi_H$, and their correlation.

Subsequently, the assist oscillator generation portion 150 generates an assist oscillator z on the basis of the second oscillator $y_i$ generated by the second oscillator generation portion 140 (s150 in FIG. 2). Specifically, the assist oscillator z is generated according to the following expression (4).

$$z_L = p_+ y_{L+} - p_- y_{L-},$$

$$z_R = p_+ y_{R+} + p_- y_{R-} \tag{4}$$

where $p_+$ and $p_-$ are activating factors.

Then, a current $I = (I_L, I_R)$ responsive to the assist oscillator z generated by the assist oscillator generation portion 150 is supplied from the battery 208 to each of the left and right actuators 210, and a force $F = (F_L, F_R)$ corresponding to the power of the actuator 210 acts on the corresponding thigh of the user.

Thereafter, the above processes (s111, s112, s150 in FIG. 2) are repeated, whereby the user walks while being applied with the torques around the hip joints by the walking assist device 200.

According to the walking assist device 200 and its control system of the present invention which implement the above functions, firstly, the first oscillator x is generated based on the user's first motion oscillator (shoulder joint angular velocity) $d\phi_S/dt$ (s120 in FIG. 2). The first oscillator x oscillates in an autonomous rhythm reflecting the natural angular velocity $\omega_M$, while harmonizing with the rhythm of the user's first motion oscillator $d\phi_S/dt$ by virtue of the "mutual entrainment" effect which is one of the properties of the van der Pol equation (see the expression (1)). Meanwhile, the first oscillator x may have an inappropriate phase difference relative to the user's first motion oscillator $d\phi_S/dt$ from the viewpoint of matching the user's motion rhythm with a target rhythm while harmonizing the user's motion rhythm with the assist rhythm made by the walking assist device 200. As such, if the assist oscillator z is directly generated from the first oscillator x, there is a possibility that the user's walking rhythm assisted by the assist oscillator z may deviate from the target rhythm.

Therefore, a new natural angular velocity $\omega_M$ is set according to the first phase difference $\delta\theta_1$ which is the phase difference between the user's first motion oscillator $d\phi_S/dt$ and the first oscillator x (s130 in FIG. 2). Accordingly, the new natural angular velocity $\omega_M$ becomes equivalent to an angular velocity of an appropriate oscillator from the viewpoint of assisting the user's motion in such a way as to match the user's motion rhythm with the target rhythm, while harmonizing with the user's motion rhythm identified by the first motion oscillator $d\phi_S/dt$. Thereafter, generation of a new first oscillator x in such a way as to reflect a new natural angular velocity $\omega_M$ (s120 in FIG. 2) is repeated, which can gradually reduce the deviation of the phase difference (first phase difference) $\delta\theta_1$ between the first motion oscillator $d\phi_S/dt$ and the first oscillator x from the target phase difference $\delta\theta_0$, while harmonizing the rhythm of the first motion oscillator $d\phi_S/dt$ with the rhythm of the first oscillator x.

Subsequently, the second oscillator y is generated on the basis of the user's second motion oscillator (hip joint angle) $\phi_H$ (s140 in FIG. 2). The second oscillator y oscillates in a rhythm reflecting the new natural angular velocity $\omega_M$ (which rhythm is specified by a time constant $\tau_{1i}$ of the second element i). Then, the assist oscillator z is generated on the basis of the second oscillator y, whereby the force F responsive to the assist oscillator z is applied to the user's body (s150 in FIG. 2).

As described above, the assist oscillator z is generated in such a way as to reflect the motion rhythms of the different body parts, i.e., upper limb (arm (particularly, the upper arm)) and lower limb (leg (particularly, the thigh)). As such, the user's motion can be assisted in such a way as to bring the user's motion rhythm close to the target rhythm, while harmonizing the motion rhythms of the upper and lower limbs corresponding to the user's first motion oscillator (shoulder joint angular velocity) $d\phi_S/dt$ and the second motion oscillator (hip joint angle) $\phi_H$. With the total harmonization of the motion rhythms of the user's upper and lower limbs and the rhythm of the assist oscillator, the assist rhythm made by the walking assist device 200 is harmonized with the user's motion rhythm, and the user's motion rhythm is also harmonized with the assist rhythm by the walking assist device 200, and therefore, harmonization (mutual adaptation) is established between the user (human) and the device (machine).

As described above, according to the walking assist device 200 of the present invention, the user's motion can be assisted in an appropriate rhythm from the viewpoint of bringing the user's motion rhythm close to its target rhythm, while totally harmonizing the motion rhythms of the different parts of the user's body and the rhythm of assisting the user's motion.

In the case where the upper limb corresponds to a non-impaired body part suffering no motor dysfunction and the lower limb corresponds to an impaired body part suffering motor dysfunction, the effect of mutual adaptation is implemented where the movement of the upper limb (forward/backward swinging motion of the upper arm) harmonizes with the movement of the lower limb (forward/backward motion of the thigh) while the movement of the lower limb is being governed by the movement of the upper limb.

Further, in the case where the lower limb corresponds to a non-impaired body part suffering no motor dysfunction and the upper limb corresponds to an impaired body part suffering motor dysfunction, the effect of mutual adaptation is implemented where the movement of the lower limb (forward/backward motion of the thigh) harmonizes with the movement of the upper limb (forward/backward swinging motion of the upper arm) while the movement of the upper limb is being governed by the movement of the lower limb.

Furthermore, it is possible to cause the qualitative relationship between a plurality of actual elements concerning the user's actual motion to be reflected to the relationship between a plurality of virtual first elements in the first model (see the expression (1)). Moreover, the relationship between the first elements (first correlation coefficient g) may be adjusted based on part or all of the scales and rhythms of the first motion oscillator $d\phi_S/dt$ and the second motion oscillator $\phi_H$ corresponding to the movements of the user's upper and lower limbs, respectively, and their correlation. Accordingly, an appropriate first oscillator x can be generated in view of the relationship between the plurality of actual elements which is reflected, e.g., to the rhythms of the first motion oscillator $d\phi_S/dt$ and the second motion oscillator $\phi_H$ (s120 in FIG. 2).

For example, in the case where the left and right upper limbs are assumed as the plurality of actual elements, the first oscillator x is generated so as to reflect the qualitative relationship between the left and right upper limbs such as in moving back and forth alternately or the like. Accordingly, the rhythm of the assist oscillator z assisting the user's motion can be made appropriate in view of the relationship concerned.

Furthermore, it is possible to cause the relationship between the plurality of actual elements concerning the user's actual motion to be reflected to the relationship between a plurality of virtual second elements in the second model (see the expression (3)). Moreover, the relationship between the plurality of second elements (second correlation coefficient $w_{i/j}$) may be adjusted based on part or all of the scales and rhythms of the first motion oscillator $d\phi_S/dt$ and the second motion oscillator $\phi_H$ corresponding to the movements of the user's upper and lower limbs, respectively, and their correlation. Accordingly, an appropriate second oscillator y can be generated in view of the relationship between the plurality of actual elements which is reflected, e.g., to the rhythms of the first motion oscillator $d\phi_S/dt$ and the second motion oscillator $\phi_H$ (s140 in FIG. 2) For example, in the case where a plurality of user's neurons are assumed as a plurality of actual elements, the second oscillator y is generated so as to reflect the qualitative relationship or the like between the plurality of neurons which govern the motions of the different body parts. Therefore, the rhythm of the assist oscillator z assisting the user's motion can be made appropriate in view of the relationship concerned.

Experimental results of the operation and effect of the walking assist device 200 according to the present invention will now be described with reference to FIGS. 5 and 6. The experiment was carried out in the state where the movements of the left and right lower limbs which are impaired and suffering motor dysfunction are assisted in a manner reflecting the first motion oscillator (shoulder joint angular velocity) $d\phi_S/dt$ corresponding to the movements of the left and right upper limbs which are not impaired.

Figure 5:
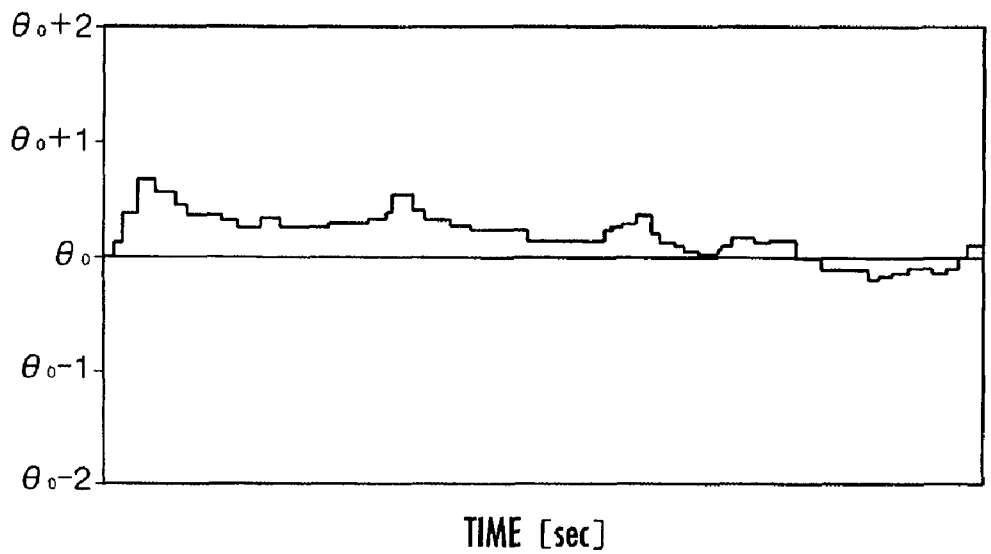
FIG. 5 is an explanatory diagram showing an experimental result of the operation and effect of the motion assist device according to the present invention.

FIG. 5 shows a change of the phase difference between the second motion oscillator (hip joint angle) $\phi_H$ and the assist oscillator z with respect to time. The relevant phase difference approximately coincides with a target phase difference $\delta\theta_0$. This means that the walking motion assist rhythm by the walking assist device 200 has been set to an appropriate rhythm from the viewpoint of harmony with the motion rhythm of the user's lower limbs (thighs) according to the target phase difference $\delta\theta_0$.

Figure 6:
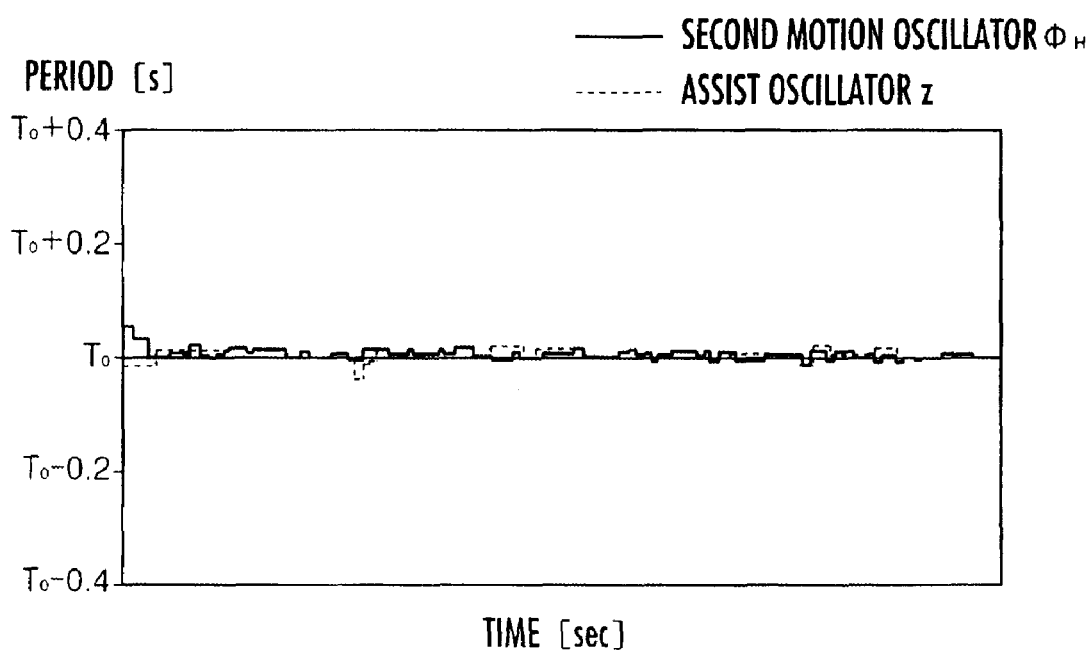
FIG. 6 is another explanatory diagram showing an experimental result of the operation and effect of the motion assist device according to the present invention.

FIG. 6 shows periods of the second motion oscillator $\phi_H$ and the assist oscillator z. The periods of both oscillators approximately coincide with a target period $T_0$ corresponding to the period of the first motion oscillator $d\phi_S/dt$. This means that the motions of the user's lower limbs (particularly, the thighs) have been assisted in an appropriate rhythm from the viewpoint of overall harmony of the motion rhythm of the user's upper limbs reflected to the first motion oscillator $d\phi_S/dt$, the motion rhythm of the lower limbs reflected to the second motion oscillator $\phi_H$, and the assist rhythm by the walking assist device 200.

In the embodiment described above, the shoulder joint angular velocity $d\phi_S/dt$ is measured as the first motion oscillator (s111 in FIG. 2), and the hip joint angle $\phi_H$ is measured as the second motion oscillator (s112 in FIG. 2). In another embodiment, any kind of oscillator that oscillates in a rhythm reflecting the motion rhythm of any part of the user's body may be measured as the first motion oscillator, which may be a shoulder joint angle, angle or angular velocity of knee joint, ankle joint, shoulder joint, elbow joint or the like, the user's landing sound, respiratory sound, intermittently generated voice sound, or the like. In this case, a joint angle or angular velocity of the body part different from that of the first motion oscillator or the landing sound may be measured as the second motion oscillator.

In the embodiment described above, the assist oscillator z is generated so as to reflect both of the rhythm of the second motion oscillator (hip joint angle) $\phi_H$ responsive to the movement of the body part (lower limb) to which the force F is applied from the walking assist device 200 and the rhythm of the first motion oscillator (shoulder joint angular velocity) $d\phi_S/dt$ responsive to the movement of the body part (upper limb) to which the force F is not applied from the walking assist device 200. As another embodiment, it may be configured such that the assist oscillator z is generated so as to reflect both of the rhythm of the first motion oscillator responsive to the movement of the body part to which the force F is applied from the walking assist device 200 and the rhythm of the second motion oscillator responsive to the movement of the body part to which the force F is not applied from the walking assist device 200.

According to the walking assist device 200 of the other embodiment, the assist oscillator is generated in a manner reflecting both of the motion rhythm of the body part to which the force F is applied by the walking assist device 200 (i.e., the rhythm of the first motion oscillator) and the motion rhythm of the body part to which the force F of the walking assist device 200 is not applied (i.e., the rhythm of the second motion oscillator).

Accordingly, for example, the movement of a body part which is impaired and suffering motor dysfunction and thus is assisted by the force F of the walking assist device 200 can be assisted in an appropriate rhythm from the viewpoint of overall harmony of the rhythm of the first motion oscillator responsive to the movement of that impaired body part, the rhythm of the second motion oscillator responsive to the movement of a non-impaired body part, and the motion assist rhythm made by the walking assist device 200. In this example, the effect of mutual adaptation is implemented where the movement of the impaired body part is harmonized with the movement of the non-impaired body part, while the movement of the non-impaired body part is being governed by the movement of the impaired body part.

Alternatively, for example, the movement of a body part which is not impaired but assisted by the force F of the walking assist device 200 can be assisted in an appropriate rhythm from the viewpoint of overall harmony of the rhythm of the first motion oscillator responsive to the movement of that non-impaired body part, the rhythm of the second motion oscillator responsive to the movement of a body part which is impaired and suffering motor dysfunction but is not assisted by the force F of the walking assist device 200, and the motion assist rhythm by the walking assist device 200. In this example, the effect of mutual adaptation is implemented where the movement of the non-impaired body part is harmonized with the movement of the impaired body part, while the movement of the impaired body part is being governed by the movement of the non-impaired body part.

In the embodiment described above, the force (torques around the hip joints) F acting on the user's left and right thighs assists the user's walking motion as a force responsive to the assist oscillator z. In another embodiment, the force F acting on any part of the user's body, such as the torque around any joint selected from among the knee joint, ankle joint, shoulder joint, elbow joint, carpal joint and the like, may assist the user's motion as a force responsive to the assist oscillator z. The combination of the joints to which the torque F is applied may be changed depending on each user.

Although an increase in type of the motion oscillators to be measured leads to an increase in number of correlation terms in the nonlinear differential equation (the expression (1)) based on the generation of the first oscillator x such as a van der Pol equation or in the nonlinear differential equation (the expression (3)) based on the generation of the second oscillator $y_i$, adjustment of the correlation coefficient enables more careful motion assistance in consideration of the movements of various parts of the user's body.

In the embodiment described above, the second oscillator y is generated according to the second model in which the natural angular velocity $\omega_{ML}$ based on the left shoulder joint angular velocity $d\phi_{SL}/dt$ is reflected to the time constants $\tau_{1L+}$, $\tau_{1L-}$ specifying the rhythms of the second oscillators $y_{L+}$, $y_{L-}$ which are outputs of the left-side second elements L+, L−, and the natural angular velocity $\omega_{MR}$ based on the right shoulder joint angular velocity $d\phi_{SR}/dt$ is reflected to the time constants $\tau_{1R+}$, $\tau_{1R-}$ specifying the rhythms of the second oscillators $y_{R+}$, $y_{R-}$ which are outputs of the right-side second elements R+, R− (see the expressions (3), (3.1), and (3.2)). In another embodiment, the second oscillator y may be generated according to the second model in which the natural angular velocity $\omega_{MR}$ based on the right shoulder joint angular velocity $d\phi_{SR}/dt$ is reflected to the time constants $\tau_{1L+}$, $\tau_{1L-}$ of the second oscillators $y_{L+}$, $y_{L-}$ which are outputs of the left-side second elements L+, L−, and the natural angular velocity $\omega_{ML}$ based on the left shoulder joint angular velocity $d\phi_{SL}/dt$ is reflected to the time constants $\tau_{1R+}$, $\tau_{1R-}$ of the second oscillators $y_{R+}$, $y_{R-}$ which are outputs of the right-side second elements R+, R−.

At the time of motion of the user such as walking or running motion, it is desirable for the user, from the viewpoint of natural body movement, that the motion rhythm of the arm (upper limb) around the left shoulder joint and the motion rhythm of the leg (lower limb) around the right hip joint maintain an approximately constant relationship, and that the motion rhythm of the arm around the right shoulder joint and the motion rhythm of the leg around the left hip joint maintain an approximately constant relationship. That is, it is desirable for the user from the viewpoint of natural walking that the movement of the left arm harmonizes with the movement of the right leg, and that the movement of the right arm harmonizes with the movement of the left leg.

In this regard, according to the walking assist device 200 of the other embodiment, the forward/backward swinging movement of the arm or the forward/backward movement of the leg can be assisted in an appropriate rhythm from the viewpoint of harmony of the motion rhythm responsive to the forward/backward swinging movement of the user's arm (particularly, the upper arm), the motion rhythm responsive to the forward/backward movement of the leg (particularly, the thigh) on the side opposite from the side of the arm, and the motion assist rhythm by the motion assist device.

In the embodiment described above, the assist oscillator z is generated according to the expression (4). In another embodiment, the assist oscillator z may be generated according to the following procedure, in order to bring the user's motion rhythm close to a target rhythm and further to bring the motion scale close to a target scale.

Specifically, firstly, a first assist oscillator $z_1$ is generated according to the following expression (5).

$$z_{1L} = g_{1+}(\omega_{ML})g_+(\phi_{HL})y_{L+} - g_{1-}(\omega_{ML})g_-(\phi_{HL})y_{L-},$$

$$z_{1R} = g_{1+}(\omega_{MR})g_+(\phi_{HR})y_{R+} - g_{1-}(\omega_{MR})g_-(\phi_{HR})y_{R-} \quad (5)$$

where "$g_{1+}$", "$g_{1-}$", "$g_+$", and "$g_-$" are functions defined according to the following expressions (5.1) to (5.4), respectively.

$$g_{1+}(\omega) = \Sigma_k a_{k+}\omega^k \; (a_{k+}: \text{coefficient}, k=0 \text{ to } 3) \quad (5.1)$$

$$g_{1-}(\omega) = \Sigma_k a_{k-}\omega^k \; (a_{k-}: \text{coefficient}, k=0 \text{ to } 3) \quad (5.2)$$

$$g_+(\phi) \equiv c_{1+}(\phi - \phi_{0+}) + c_{2+}(\phi - +\phi_{0+})^3$$

($c_{1+}, c_{2+}$: coefficient; $\phi_{0+}$: target value of hip joint angle $\phi_H$ in bending direction) (5.3)

$$g_-(\phi) = c_{1-}(\phi - \phi_{0-}) + c_{2-}(\phi - \phi_{0-})^3$$

($c_{1-}, c_{2-}$: coefficient; $\phi_{0-}$: target value of hip joint angle $\phi_H$ in stretching direction) (5.4)

Figure 7:
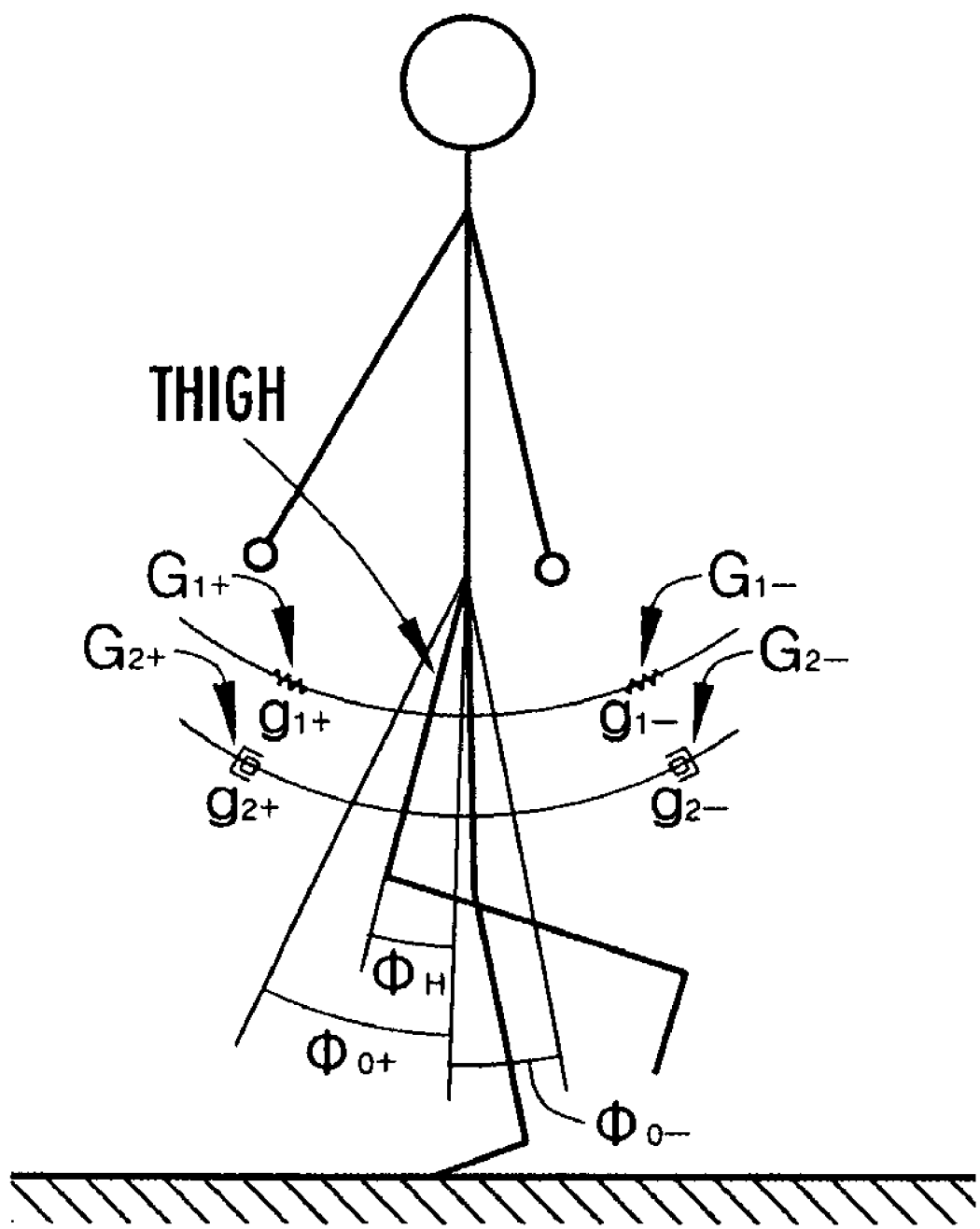
FIG. 7 is an explanatory diagram of virtual springs and dampers related to generation of assist oscillators.

The first assist oscillator $z_1$ is understood as an elastic force obtained by two virtual springs $G_{1+}$ and $G_{1-}$ shown in FIG. 7 having the first coefficients $g_{1+}$ and $g_{1-}$, respectively, as spring coefficients (elastic coefficients). The first coefficients $g_{1+}$ and $g_{1-}$ specify the gradient of a first potential (a potential of a virtual spring (elastic element)) which brings the hip joint angle (the second motion oscillator responsive to the user's motion scale) $\phi_H$ close to the target value $\phi_{0+}$ (>0) and $\phi_{0-}$ (<0) responsive to the user's target motion scale, according to the natural angular velocity $\omega_M$ (see the expressions (5.1) and (5.2)). Specifically, the first assist oscillator $z_1$ is represented as an elastic force of an elastic element such as a virtual spring or the like which has the first coefficient $g_{1+}$, $g_{1-}$ responsive to the first potential as the elastic coefficient (spring coefficient) and which restores the value of the hip joint angle $\phi_H$ to the target value $\phi_{0+}$, $\phi_{0-}$. This enables the user's motion to be assisted with the rhythm and scale reflecting the elastic elements of the user's body such as the elastic force generated during the transition from the muscle contraction state to the muscle stretch state.

The elastic force of one virtual spring $G_{1+}$ acts on the user's thigh in such a way as to bring the hip joint angle $\phi_H$ close to the target value $\phi_{0+}$ according to the spring coefficient $g_{1+}$ (see the expression (5)). Specifically, if the hip joint angle $\phi_H$ is less than the target value $\phi_{0+}$, the elastic force of the spring $G_{1+}$ acts on the thigh in such a way as to move the thigh in the direction of increasing the hip joint angle $\phi_H$ (forward). If the hip joint angle $\phi_H$ exceeds the target value $\phi_{0+}$, the elastic force of the spring $G_{1+}$ acts on the thigh in such a way as to move the thigh in the direction of decreasing the hip joint angle $\phi_H$ (backward).

Moreover, the elastic force of the other virtual spring $G_{1-}$ acts on the user's thigh in such a way as to bring the hip joint angle $\phi_H$ close to the target value $\phi_{0-}$ according to the spring coefficient $g_{1-}$ (see the expression (5)). Specifically, if the hip joint angle $\phi_H$ exceeds the target value $\phi_{0-}$, the elastic force of the spring $G_{1-}$ acts on the thigh in such a way as to move the thigh in the direction of decreasing the hip joint angle $\phi_H$ (backward). If the hip joint angle $\phi_H$ is less than the target value $\phi_{0-}$, the elastic force of the spring $G_1$ acts on the thigh in such a way as to move the thigh in the direction of increasing the hip joint angle $\phi_H$ (forward).

Furthermore, a second assist oscillator $z_2$ is generated according to the following expression (6).

$$z_{2L} = -g_{2+}(\omega_{ML})\left(\frac{d\phi_{HL}}{dt}\right)H_+(\phi_{HL})y_{L+} + g_{2-}(\omega_{ML})\left(\frac{d\phi_{HL}}{dt}\right)H_-(\phi_{HL})y_{L-}, \quad (6)$$

-continued $$z_{2R} = -g_{2+}(\omega_{MR})\left(\frac{d\phi_{HR}}{dt}\right)H_{+}(\phi_{HR})y_{R+} +$$

$$g_{2-}(\omega_{MR})\left(\frac{d\phi_{HR}}{dt}\right)H_{-}(\phi_{HR})y_{R-}$$

where "$g_{2+}$", "$g_{2-}$", "$H_{+}$", and "$H_{-}$" are functions defined according to the following expressions (6.1) to (6.4), respectively.

$$g_{2+}(\omega) \equiv \Sigma_k b_{k+} \omega^k \ (b_{k+}: \text{coefficient}, k=0 \text{ to } 3) \quad (6.1)$$

$$g_{2-}(\omega) \equiv \Sigma_k b_{k-} \omega^k \ (b_{k-}: \text{coefficient}, k=0 \text{ to } 3) \quad (6.2)$$

$$H_{+}(\phi) \equiv 1(\phi \leq 0), 0(\phi > 0) \quad (6.3)$$

$$H_{-}(\phi) \equiv 1(\phi > 0), 0(\phi \leq 0) \quad (6.4)$$

The second assist oscillator $z_2$ is understood as a damping force acting on the user's left and right thighs by two virtual dampers $G_{2+}$ and $G_{2-}$ shown in FIG. 7 having the second coefficients $g_{2+}$ and $g_{2-}$, respectively, as damper coefficients (damping coefficients). The second coefficients $g_{2+}$ and $g_{2-}$ specify the gradient of a second potential (a potential of a virtual damper (damping element)) which prevents an increase in absolute value of the hip joint angle (the second motion oscillator responsive to the user's motion scale) $\phi_H$, according to the natural angular velocity $\omega_M$ (see the expressions (6.1) and (6.2)). Specifically, the second assist oscillator $z_2$ is represented as a damping force of a damping element such as a virtual damper or the like which has the second coefficient $g_{2+}$, $g_{2-}$ responsive to the second potential as the damping coefficient (damper coefficient) and which prevents an increase in absolute value of the hip joint angle $\phi_H$, according to the hip joint angular velocity (the time derivative of the second motion oscillator responsive to the user's motion scale) $d\phi_H/dt$. This enables the user's motion to be assisted with the rhythm and scale reflecting the damping elements of the user's body such as the viscous force generated during the transition from the muscle stretch state to the muscle flexed state.

The damping force of one virtual damper $G_{2+}$ acts on the user's thigh in such a way as to prevent an increase in absolute value of the hip joint angle $\phi_H$ toward the front side (inflection side), according to the damper coefficient $g_{2+}$ and the hip joint angular velocity $d\phi_H/dt$ (see the expression (6)). In other words, the damping force of the virtual damper $G_{2+}$ acts on the thigh in such a way as to prevent the excessive forward movement of the thigh.

Moreover, the damping force of the other virtual damper $G_{2-}$ acts on the user's thigh in such a way as to prevent an increase in absolute value of the hip joint angle $\phi_H$ toward the back side (stretch side), according to the damper coefficient $g_{2-}$ and the hip joint angular velocity $d\phi_H/dt$ (see the expression (6)). In other words, the damping force of the virtual damper $G_{2+}$ acts on the thigh in such a way as to prevent the excessive backward movement of the thigh.

Furthermore, the second assist oscillator $z_2$ includes step functions $H_{+}$ and $H_{-}$ as the functions of the hip joint angle $\theta H$. Therefore, it is possible to avoid such a situation that the damping forces of the two virtual dampers $G_{2+}$ and $G_{2-}$ cancel out each other.

The assist oscillator $z$ (=$z_1$+$z_2$) is generated by combination of the first assist oscillator $z_1$ and the second assist oscillator $z_2$ generated by the assist oscillator generation portion 150.

According to the walking assist device 200 of the other embodiment, the user's walking motion or any other motion can be assisted in such a way as to bring the user's motion scale close to the target scale, for the following reasons.

The first coefficients $g_{1+}$ and $g_{1-}$ included in the first assist oscillator $z_1$ are provided according to the first potential (the potential of the virtual elastic elements) for bringing the user's hip joint angle $\phi_H$ close to the target values $\phi_{0+}$ and $\phi_{0-}$. The first coefficients $g_{1+}$ and $g_{1-}$ are provided according to the natural angular velocity $\omega_M$ (=angular velocity $\omega_m$ of the virtual assist oscillator $\theta_m$) (see the expressions (5.1) and (5.2)). The natural angular velocity (a corresponds to an angular velocity of an appropriate oscillator from the viewpoint of assisting the user's motion in such a way as to match the user's motion rhythm with the target rhythm while harmonizing with the user's motion rhythm, as described above.

Moreover, the second coefficients $g_{2+}$ and $g_{2-}$ included in the second assist oscillator $z_2$ are provided according to the second potential (the potential of the virtual damping elements) for preventing an increase in absolute value of the user's hip joint angle $\phi_H$. The second coefficients $g_{2+}$ and $g_{2-}$ are provided according to the natural angular velocity $\omega_M$ (see the expressions (6.1) and (6.2)). The natural angular velocity $\omega_M$ corresponds to an angular velocity of an appropriate oscillator from the viewpoint of assisting the user's motion in such a way as to match the user's motion rhythm with the target rhythm while harmonizing with the user's motion rhythm, as described above.

Therefore, the first assist oscillator $z_1$ is generated so as to reflect the first coefficients $g_{1+}(\omega_M)$ and $g_{1-}(\omega_M)$ according to the natural angular velocity $\omega_M$ and the second assist oscillator $z_2$ is generated so as to reflect the second coefficients $g_{2+}(\omega_M)$ and $g_{2-}(\omega_M)$ according to the natural angular velocity $\omega_M$, whereby the user's motion can be assisted in such a way as to bring the user's motion scale close to the target scale, while harmonizing the user's motion rhythm with the rhythm of the assist oscillator $z$ and further matching the user's motion rhythm with the target rhythm.

The target values $\phi_{0+}$ and $\phi_{0-}$ of the hip joint angle $\phi_H$ may be set in accordance with a target "stride" set by the user via an operation of a setting button (not shown) provided in the walking assist device 200, according to geometrical conditions for the posture of the user's leg, including the hip joint angle $\phi_H$.

Further, the coefficients $a_{k+}$ and $a_{k-}$ included respectively in the first coefficients $g_{1+}(\omega_M)$ and $g_{1-}(\omega_M)$ which are the functions of the natural angular velocity $\omega_M$ may be set on the basis of part or all of the scales and rhythms of the first and second motion oscillators and correlation thereof. In this manner, the user's motion can be assisted with the rhythm and scale reflecting the properties of the elastic elements of the user's body, such as the elastic force generated during the transition from the muscle contraction state to the muscle stretch state, which are reflected to part or all of the scales and rhythms of the first and second motion oscillators and correlation thereof.

Furthermore, the coefficients $b_{k+}$ and $b_{k-}$ included respectively in the second coefficients $g_{2+}(\omega_M)$ and $g_{2-}(\omega_M)$ which are the functions of the natural angular velocity $\omega_M$ may be set on the basis of part or all of the scales and rhythms of the first and second motion oscillators and correlation thereof. In this manner, the user's motion can be assisted with the rhythm and scale reflecting the properties of the damping elements of the user's body, such as the viscous force generated during the transition from the muscle stretch state to the muscle flexed state, which are reflected to part or all of the scales and rhythms of the first and second motion oscillators and correlation thereof.

The control system of the walking assist device 200 as another embodiment of the present invention may further include a state measurement portion which measures one or both of the user's motion state and physiological state, and a target phase difference setting portion which sets a target phase difference $\delta\theta_0$ according to one or both of the user's motion state and physiological state determined by the state measurement portion. The user's "motion state" may include an upward walking state where the user ascends a slope or stairs, a level walking state where the user walks on the substantially level ground, a downward walking state where the user descends a slope or stairs, a quick walking state where the user walks quickly, and a slow walking state where the user walks slowly. Additionally, the user's "physiological state" may include a state where the user's degree of fatigue is high, a state where the user's degree of fatigue is low, a state where the user's heart rate or perspiration amount is high, a state where the user's heart rate is low, and the like.

According to the motion assist device having the above configuration, the user's motion can be assisted in such a way that the phase difference between the user's shoulder joint angular velocity (first motion oscillator) $d\phi_S/dt$ and the first oscillator x approaches a target phase difference $\delta\theta_0$ according to the user's "walking state". Accordingly, the user's motion is assisted in an appropriate rhythm from the viewpoint of bringing the user's motion rhythm close to the target rhythm according to a change of the user's walking state.

The user's walking state (motion state) can be measured, for example, through the following procedure.

Correspondence between the user's walking state and a track pattern formed on an n-dimensional space by n motion oscillators is read from a memory. Thereafter, the user's "walking state" is measured on the basis of the correspondence and the track pattern formed on the n-dimensional space by the n motion oscillators including the hip joint angle $\phi_H$ measured by the motion oscillator measurement portion 110. As the motion oscillator for use in measurement of the walking state, any kind of parameter varying with a rhythm linked to the walking rhythm may be measured, which may be the user's hip joint angular velocity $d\phi_H/dt$, the angle, angular velocity, or angular acceleration of the knee joint, ankle joint, shoulder joint, or elbow joint, the position of a portion of a leg, or the walker's landing sound, respiratory sound, intentional voice sound, or the like.

The invention claimed is:

1. A motion assist device for assisting a user's motion by applying a force varying with respect to time in accordance with an assist oscillator to a user's body, comprising:
   a motion oscillator measurement element configured to measure motion oscillators serving as parameters that vary with respect to time responsive to movements of two different body parts of the user as first and second motion oscillators, respectively;
   a first oscillator generation element configured to generate a first oscillator as a first output oscillation signal by inputting the first motion oscillator measured by the motion oscillator measurement element to a first model as a first input oscillation signal, the first model being for generating the first output oscillation signal that attains mutual entrainment with the first input oscillation signal and varies with respect to time at an angular velocity determined according to a natural angular velocity;
   a natural angular velocity setting element configured to newly set the natural angular velocity in such a way as to bring a first phase difference corresponding to a phase difference between the first motion oscillator measured by the motion oscillator measurement element and the first oscillator generated by the first oscillator generation element close to a target phase difference;
   a second oscillator generation element configured to generate a second oscillator as a second output oscillation signal by inputting the second motion oscillator measured by the motion oscillator measurement element to a second model as a second input oscillation signal, the second model being for generating the second output oscillation signal that varies with respect to time at an angular velocity determined according to the natural angular velocity set by the natural angular velocity setting element on the basis of the input oscillation signal; and
   an assist oscillator generation element configured to generate the assist oscillator on the basis of the second oscillator generated by the second oscillator generation element,
   wherein the motion oscillator measurement element is configured to measure a joint angle of an upper limb of the user or its time derivative as the first motion oscillator and a joint angle of a lower limb of the user or its time derivative as the second motion oscillator, or to measure a joint angle of a lower limb of the user or its time derivative as the first motion oscillator and a joint angle of an upper limb of the user or its time derivative as the second motion oscillator.

2. A motion assist device for assisting a user's motion by applying a force varying with respect to time in accordance with an assist oscillator to a user's body, comprising:
   a motion oscillator measurement element configured to measure motion oscillators serving as parameters that vary with respect to time responsive to movements of two different body parts of the user as first and second motion oscillators, respectively;
   a first oscillator generation element configured to generate a first oscillator as a first output oscillation signal by inputting the first motion oscillator measured by the motion oscillator measurement element to a first model as a first input oscillation signal, the first model being for generating the first output oscillation signal that attains mutual entrainment with the first input oscillation signal and varies with respect to time at an angular velocity determined according to a natural angular velocity;
   a natural angular velocity setting element configured to newly set the natural angular velocity in such a way as to bring a first phase difference corresponding to a phase difference between the first motion oscillator measured by the motion oscillator measurement element and the first oscillator generated by the first oscillator generation element close to a target phase difference;
   a second oscillator generation element configured to generate a second oscillator as a second output oscillation signal by inputting the second motion oscillator measured by the motion oscillator measurement element to a second model as a second input oscillation signal, the second model being for generating the second output oscillation signal that varies with respect to time at an angular velocity determined according to the natural angular velocity set by the natural angular velocity setting element on the basis of the input oscillation signal; and
   an assist oscillator generation element configured to generate the assist oscillator on the basis of the second oscillator generated by the second oscillator generation element, wherein
the second model is a model in which an angular velocity of the second output oscillation signal serving as a basis for the assist oscillator that determines a force to be applied to a left leg of the user is determined according to the natural angular velocity that is set by the natural angular velocity setting element on the basis of the first motion oscillator as a parameter varying with respect to time in accordance with movement of a right arm of the user, and in which an angular velocity of the second output oscillation signal serving as a basis for the assist oscillator that determines a force to be applied to a right leg of the user is determined according to the natural angular velocity that is set by the natural angular velocity setting element on the basis of the first motion oscillator as a parameter varying with respect to time in accordance with movement of a left arm of the user, and
the second oscillator generation element is configured to generate the second oscillator oscillating according to the second model.

3. A motion assist device for assisting a user's motion by applying a force varying with respect to time in accordance with an assist oscillator to a user's body, comprising:
a motion oscillator measurement element configured to measure motion oscillators serving as parameters that vary with respect to time responsive to movements of two different body parts of the user as first and second motion oscillators, respectively;
a first oscillator generation element configured to generate a first oscillator as a first output oscillation signal by inputting the first motion oscillator measured by the motion oscillator measurement element to a first model as a first input oscillation signal, the first model being for generating the first output oscillation signal that attains mutual entrainment with the first input oscillation signal and varies with respect to time at an angular velocity determined according to a natural angular velocity;
a natural angular velocity setting element configured to newly set the natural angular velocity in such a way as to bring a first phase difference corresponding to a phase difference between the first motion oscillator measured by the motion oscillator measurement element and the first oscillator generated by the first oscillator generation element close to a target phase difference;
a second oscillator generation element configured to generate a second oscillator as a second output oscillation signal by inputting the second motion oscillator measured by the motion oscillator measurement element to a second model as a second input oscillation signal, the second model being for generating the second output oscillation signal that varies with respect to time at an angular velocity determined according to the natural angular velocity set by the natural angular velocity setting element on the basis of the input oscillation signal; and
an assist oscillator generation element configured to generate the assist oscillator on the basis of the second oscillator generated by the second oscillator generation element,
wherein
the first model is expressed by a first system of simultaneous equations including a term in which a respective one of a plurality of the first output oscillation signals that attain mutual entrainment with a corresponding one of a plurality of the first input oscillation signals and vary with respect to time at an angular velocity determined according to the natural angular velocity is multiplied by a first correlation coefficient,
the motion oscillator measurement element is configured to measure a plurality of the first motion oscillators, and
the first oscillator generation element is configured to generate a plurality of the first oscillators as the plurality of first output oscillation signals by inputting to the first model the plurality of first motion oscillators measured by the motion oscillator measurement element as the plurality of first input oscillation signals, while adjusting the first correlation coefficient on the basis of part or all of amplitudes and angular velocities of the first and second motion oscillators measured by the motion oscillator measurement element.

4. A motion assist device for assisting a user's motion by applying a force varying with respect to time in accordance with an assist oscillator to a user's body, comprising:
a motion oscillator measurement element configured to measure motion oscillators serving as parameters that vary with respect to time responsive to movements of two different body parts of the user as first and second motion oscillators, respectively;
a first oscillator generation element configured to generate a first oscillator as a first output oscillation signal by inputting the first motion oscillator measured by the motion oscillator measurement element to a first model as a first input oscillation signal, the first model being for generating the first output oscillation signal that attains mutual entrainment with the first input oscillation signal and varies with respect to time at an angular velocity determined according to a natural angular velocity;
a natural angular velocity setting element configured to newly set the natural angular velocity in such a way as to bring a first phase difference corresponding to a phase difference between the first motion oscillator measured by the motion oscillator measurement element and the first oscillator generated by the first oscillator generation element close to a target phase difference;
a second oscillator generation element configured to generate a second oscillator as a second output oscillation signal by inputting the second motion oscillator measured by the motion oscillator measurement element to a second model as a second input oscillation signal, the second model being for generating the second output oscillation signal that varies with respect to time at an angular velocity determined according to the natural angular velocity set by the natural angular velocity setting element on the basis of the input oscillation signal; and
an assist oscillator generation element configured to generate the assist oscillator on the basis of the second oscillator generated by the second oscillator generation element,
wherein
the second model is expressed by a second system of simultaneous equations including a term in which a respective one of a plurality of the second output oscillation signals that are based on a plurality of the second input oscillation signals and oscillate at an angular velocity determined according to the natural angular velocity set by the natural angular velocity setting element is multiplied by a second correlation coefficient,
the motion oscillator measurement element is configured to measure a plurality of the second motion oscillators, and
the second oscillator generation element is configured to generate a plurality of the second oscillators as the plurality of second output oscillation signals by inputting the plurality of second motion oscillators measured by the motion oscillator measurement element to the second model as the plurality of second input oscillation signals, while adjusting the second correlation coefficient on the basis of part or all of amplitudes and angular velocities of the first and second motion oscillators measured by the motion oscillator measurement element.

5. A motion assist device for assisting a user's motion by applying a force varying with respect to time in accordance with an assist oscillator to a user's body, comprising:

a motion oscillator measurement element configured to measure motion oscillators serving as parameters that vary with respect to time responsive to movements of two different body parts of the user as first and second motion oscillators, respectively;

a first oscillator generation element configured to generate a first oscillator as a first output oscillation signal by inputting the first motion oscillator measured by the motion oscillator measurement element to a first model as a first input oscillation signal, the first model being for generating the first output oscillation signal that attains mutual entrainment with the first input oscillation signal and varies with respect to time at an angular velocity determined according to a natural angular velocity;

a natural angular velocity setting element configured to newly set the natural angular velocity in such a way as to bring a first phase difference corresponding to a phase difference between the first motion oscillator measured by the motion oscillator measurement element and the first oscillator generated by the first oscillator generation element close to a target phase difference;

a second oscillator generation element configured to generate a second oscillator as a second output oscillation signal by inputting the second motion oscillator measured by the motion oscillator measurement element to a second model as a second input oscillation signal, the second model being for generating the second output oscillation signal that varies with respect to time at an angular velocity determined according to the natural angular velocity set by the natural angular velocity setting element on the basis of the input oscillation signal; and an assist oscillator generation element configured to generate the assist oscillator on the basis of the second oscillator generated by the second oscillator generation element, wherein the motion oscillator measurement element is configured to measure the second motion oscillator as a parameter which varies with respect to time in accordance with a motion of the user and which represents a motion scale of the user, and the assist oscillator generation element is configured to generate an assist oscillator which includes a first assist oscillator representing an elastic force of a virtual elastic element for bringing the second motion oscillator measured by the motion oscillator measurement element close to a target value determined responsive to a target motion scale of the user according to the second oscillator generated by the second oscillator generation element and the natural angular velocity set by the natural angular velocity setting element.

6. The motion assist device according to claim 5, wherein the assist oscillator generation element is configured to generate the first assist oscillator which includes an oscillator calculated as a product of a first coefficient which serves as an elastic coefficient of the virtual elastic element and is a function of the natural angular velocity set by the natural angular velocity setting element, a function of a deviation between a value of the second motion oscillator and a target value, and the second oscillator, while setting the first coefficient on the basis of part or all of amplitudes and angular velocities of the first and second motion oscillators measured by the motion oscillator measurement element.

7. The motion assist device according to claim 5, wherein the assist oscillator generation element is configured to generate an assist oscillator which includes a second assist oscillator representing a damping force by a virtual damping element for preventing an increase in absolute value of the second motion oscillator according to the natural angular velocity set by the natural angular velocity setting element and a time derivative of the second motion oscillator measured by the motion oscillator measurement element.

8. The motion assist device according to claim 7, wherein the assist oscillator generation element is configured to generate the second assist oscillator which includes an oscillator calculated as a product of a second coefficient which serves as a damping coefficient of the virtual damping element and is a function of the natural angular velocity set by the natural angular velocity setting element, a function of the time derivative of the second motion oscillator, and the second oscillator, while setting the second coefficient on the basis of part or all of amplitudes and angular velocities of the first and second motion oscillators measured by the motion oscillator measurement element.

* * * * *